United States Patent [19]

Redus et al.

[11] Patent Number: 4,836,032
[45] Date of Patent: Jun. 6, 1989

[54] METHOD OF DETERMINING THE QUALITY OF STEAM FOR STIMULATING HYDROCARBON PRODUCTION

[75] Inventors: Clifford L. Redus, Katy; Sze-Foo Chien; Peter L. Sigwardt, both of Houston, all of Tex.

[73] Assignee: Texaco, Inc., White Plains, N.Y.

[21] Appl. No.: 164,682

[22] Filed: Mar. 7, 1988

[51] Int. Cl.$^4$ ............................................. G01F 1/74
[52] U.S. Cl. .................................. 73/861.04; 73/29
[58] Field of Search ............... 73/29, 861.04, 195, 73/196, 861.61

[56] References Cited

U.S. PATENT DOCUMENTS

| | | | |
|---|---|---|---|
| 4,149,403 | 4/1979 | Muedary | 73/29 |
| 4,576,036 | 3/1986 | Huang et al. | 73/29 |
| 4,576,043 | 3/1986 | Nguyen | 73/861.04 |
| 4,706,492 | 11/1987 | Jones, Jr. | 73/196 |

Primary Examiner—Herbert Goldstein
Attorney, Agent, or Firm—Robert A. Kulason; James J. O'Louhlin; Robert B. Burns

[57] ABSTRACT

The use of an orifice plate in series with a critical flow choke provides a method of measurement for both steam quality and mass flowrate. Neither the orifice plate or the choke alone can be used to measure steam quality and mass flowrate. However, an expression for steam quality through both devices is obtained by solving an independent mass flowrate equation for each device—an equation for wet steam through the critical flow choke and an equation for wet steam through a sharp edged orifice plate.

5 Claims, 2 Drawing Sheets

METHOD OF DETERMINING THE QUALITY OF STEAM FOR STIMULATING HYDROCARBON PRODUCTION

BACKGROUND OF THE INVENTION

Field of the Invention

This invention concerns a method for measuring the quality of a steam flow to a well or the like. It relates more particularly to determining the quality of wet steam used for enhancing petroleum recovery from a subterranean reservoir, which steam has a relatively low quality due to the presence of water with the steam's vaporous component.

Steam flooding has become an accepted practice in oil or petroleum recovery from marginal fields or reservoirs that require a degree of stimulation to produce a satisfactory flow of the crude petroleum. Thus, a pressing need for a simple method to determine the quality of steam at the well head of an injection well has escalated. Such a measurement, if simplified, would be particularly useful toward determining the degree of heat which is put into an underground reservoir from an external source.

The measurement or monitoring of steam quality is of importance since the steam's quality directly affects production operations. Further, the quality of the steam which can be most economically injected into a particular substrate or reservoir is contingent on a number of circumstances. The latter include for one thing, the age of the reservoir and the anticipated prospects for extracting commercially justified amounts of hydrocarbons therefrom.

In brief, it is desirable that the quality of steam which is injected into each well be altered or adjusted to a level of quality that best conforms to that well's condition.

It is known to be particularly effective in this type of stimulation operation to have the flow of injected steam monitored by use of a meter positioned in the steam carrying line. It can be appreciated, that the steam will normally leave the steam generator or source at a known quality pressure and mass flow rate. As the pressurized steam flow progresses toward an injection well, however, the quality, will usually be substantially decreased. A decrease in quality can be based on such factors as the distance between the well and the source and the degree of pipe insulation. It will further depend on the number and orientation of fittings through which the stream has to travel prior to reaching the injection port or well because of phase separation that can occur in those devices.

It is important therefore as a matter of economic practicality, that a flow monitoring and controlling means be inserted into the steam carrying conduit immediately upstream of each well head. A choke mechanism in the steam line will usually function to constrict the steam flow, whereby to allow regulation of the steam mass flow rate which enters that particular well.

BRIEF SUMMARY OF THE INVENTION

The invention concerns a method and apparatus for measuring the steam quality (mass of steam vapor divided by the total mass of water and steam vapor) of wet steam having an unknown water content. The invention comprises in brief, a method and apparatus to determine the quality of product stimulation wet steam which is injected into a well for producing hydrocarbon liquid. The method is hinged on the determination of certain characteristics of the steam at the well head. Knowing these characteristics will permit the desired quality determination to be made and thereafter appropriate adjustments to the steam quality.

More precisely, the method and apparatus are addressed to measuring steam quality and adjusting flow rate to a desired degree in a steam line, prior to injection of the flow into a hydrocarbon containing substrate.

Stated another way, in any process involving steam injection to foster a secondary oil recovery procedure, a persistent problem exists in the rapid, accurate and determination of the quality and mass flow rate of steam being injected into an individual well or a group of wells. Such knowledge is relevant to production efficiency because the steam quality and mass flow rate directly affect the production operation at the production well, and consequently the investment requirements for similar steam flooding projects.

It is known to be desirable and highly practical from an economic consideration, to mix water with a high quality steam, for achieving lower quality steam at each specific well head. In such an instance, the present invention provides for means and method to quickly and accurately determine both the quality of the steam, and its mass flow rate.

It has been determined for instance that at a typical crude oil productive field, over 20,000 equivalent barrels of oil per day can be burned to provide high quality wet steam to field well patterns. The cost efficiency of this type of steam flood operation can be improved noticeably by economizing the distribution of the steam.

Steam quality tapering, and conversion to hot water floods at various field well patterns, have mandated the accurate measurement of steam quality and mass flow rates at individual injection wells. Also, the phenomena of two phase flow in conductors, as well as phase splitting, have caused steam qualities and mass rates at injection wells to be greater or less than the desired quantities to be utilized for effective reservoir management.

It is therefore an object of this invention to provide a method and apparatus for determining the quality of steam which is injected into a reservoir as the stimulating media in a steam flooding or steam stimulation operation.

A further object is to provide a method and apparatus for readily determining the quality and the mass flow rate of wet steam being injected into a hydrocarbon holding reservoir, whereby to improve the hydrocarbon production efficiency.

A still further object is to provide means for measuring the quality and adjusting the flow rate of steam under critical flow, which is injected into a hydrocarbon producing substrate by way of a critical flow choke which regulates steam flow entering the producing well.

Figure 1:
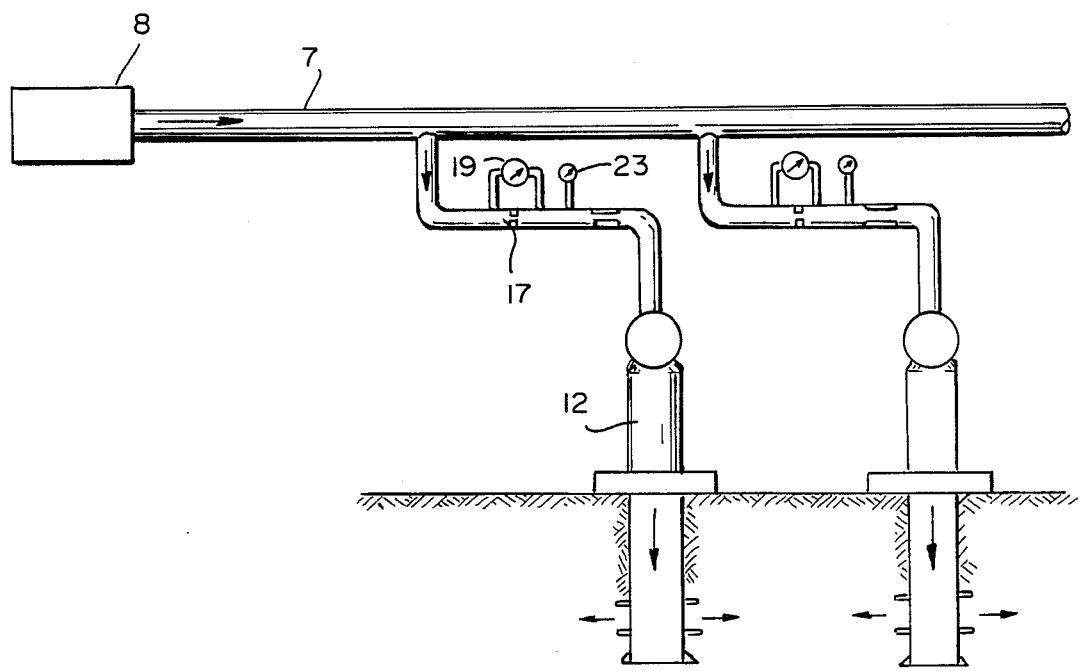
FIG. 1 is a schematic representation of the present invention as incorporated in a steam line.

The invention briefly stated, and referring to FIG. 1, relates to a method and apparatus for determining the quality and the mass flow rate of a low quality steam flow. This determination is usually made immediately prior to the steam being injected into a subterranean, hydrocarbon containing reservoir 6, by way of a steam carrying conductor 7 which is communicated with a source, or steam generator 8. The quality measuring apparatus includes a conduit 10 which carries a pressurized flow of steam from conductor 7, to a particular well head 12 which may be one well 13 in a pattern of wells.

Figure 2:
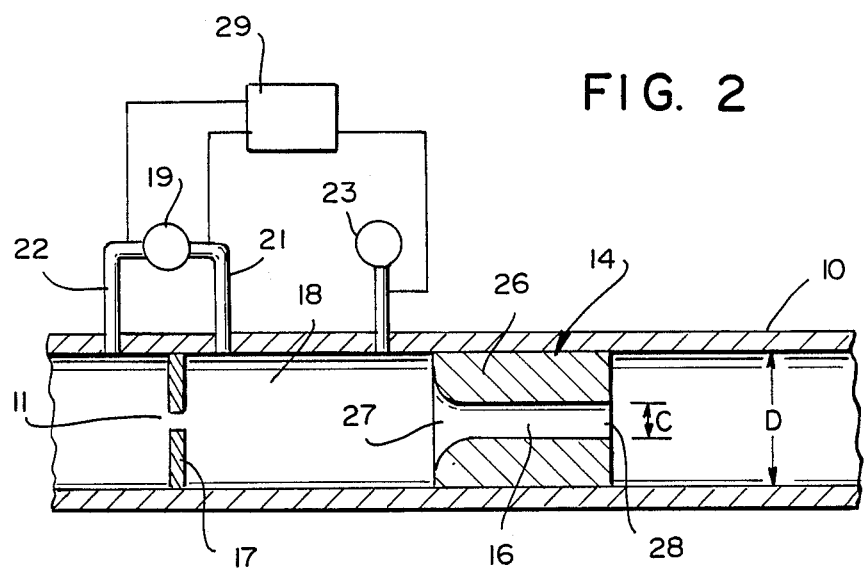
FIG. 2 is an enlarged view of one portion of the present steam quality measuring apparatus.

Referring to FIG. 2, conduit 10 is furnished with a choke 14 positioned in said conduit, having a central flow passage or bean 16 of sufficient diameter to constrict the pressurized steam to assure or provide critical flow. The apparatus further includes sharp edged orifice plate 17 which is fastened in conduit 10 and spaced upstream of choke 14.

Appropriate instrumentation communicated with passage 18 of conduit 10 provides an accurate determination of the pressure and temperature at spaced apart points in conduit 10.

Differential pressure readings at meter 19 are determined through pressure taps 21 and 22, respectively. Steam pressure is measured at pressure meter 23, located between the chock 14 inlet, and orifice plate 17. The differential pressure registered across orifice 17, and the steam pressure at choke 14 inlet, when inserted into an emperical formula, afford a quick, accurate reading of the steam's quality and its mass flow rate.

The orifice plate 17, choke 14 combination and arrangement thereof is applicable for measuring steam quality and mass flow rate at injection wells in which the critical flow choke 14 is utilized primarily to control the steam injection rate.

Again referring to FIG. 1, there is shown normally insulated steam flow pipeline 7 which includes fittings, couplings, flanges and the like and into which a flow of steam is directed from a pressurized source 8. Steam from source 8 can be of a quality between 10 and 80%, a mass flow rate from 100 to 400 barrels of steam per day cold water equivalent (BSPD-CWE), and at a pressure between 300-700 psig. Even though the empirical correction was tested over these operating conditions, the device will work over flow rate ranges from 50 to 5000 BSPD-CWE and pressures from 100 to 3000 psig with appropriate modification of the empirical constants. The first restriction in conduit 10 is comprised of sharp edged plate type orifice 17 having a central opening 11 through which the low quality steam passes.

At a point downstream of said first restriction or orifice plate 17, choke 14 is positioned which is comprised of an elongated body 26 having an inwardly convergent inlet 27 or a square edged inlet if the discharge coefficient of the choke equation is modified. The latter terminates in the elongated flow passage or bean 16. The function of choke 14 in this type of steam injection operations is to constrict the flow of steam passing therethrough to a reduced diameter, thereby to cause the flow at the choke downstream or discharge side 28 to be critical.

Operationally, as steam issues from the high pressure source 8, it will be at a known quality depending primarily on its water content. For example, the greater the percentage of water intermixed with the vaporous phase, the lesser will be the quality of the steam.

Since the steam quality will be subject to reduction in any conductor that carries the hot flow, conductor 7 is provided with a suitable insulating jacket or cover to minimize heat loss through the conductor's metallic walls.

As noted herein, the use of orifice plate 17 in series with critical flow choke 14, provides a rapid and accurate method for measurement for both steam quality and mass flowrate. Neither orifice plate 17 nor choke 14 when acting alone, is capable of measuring steam quality and mass flowrate in the presently disclosed manner. However, an expression or empirical formula for steam quality through both said devices is obtained by solving an independent mass flowrate equation for each device as follows: A first equation (3) for wet steam through critical flow choke 14, and a second equation (4) for wet steam which flows across sharp edged orifice plate 17.

In the following development of equations used in determining steam quality and flow rate, the following terms apply.

$a$ = Empirical constant in equation (7) (dimensionless)
$b$ = Empirical constant in equation (7) (dimensionless)
$c$ = Choke bore diameter (in.)
$C_f$ = Generator feedwater conductivity (micromhos/cm)
$C_o$ = Discharge coefficient of orifice plate (dimensionless)
$C_s$ = Generator steam condensate conductivity (micromhos/cm)
$C_1, C_2$ = Coefficients in equation (5)
$d$ = Diameter of orifice plate (in.)
$D$ = Inside diameter of meter run (in.)
$G^*$ = Critical mass velocity in choke (lbm/ft$^2$-sec)
$P$ = Absolute pressure upstream of choke (psia)
$r$ = Pressure ratio across orifice (dimensionless)
$W$ = Mass flowrate through device (bspd-cwe)
$X$ = No slip steam quality upstream of choke (fraction)
$m$ = Measured steam quality upstream of choke (fraction)
$Y$ = Steam vapor expansion factor (dimensionless)
$\phi$ = Differential pressure across the orifice (in. of water)
$v_l$ = Specific volume of saturated water @ pressure P (ft$^3$/lbm)
$v_g$ = Specific volume of saturated steam @ pressure P (ft$^3$/lbm)
$\gamma$ = Specific heat ratio (dimensionless).

DEVELOPMENT OF CHOKE 14 EQUATION (1)

The Napier[1] equation for critical flow through a choke modified for wet steam by King and Crocker[2] is $$G^* = 2.057 \frac{P}{X^{0.5}}, \tag{1}$$

where G* is the critical mass velocity in choke 14, P is the absolute pressure upstream of choke 14, at pressure meter 23, and X is steam quality upstream of the choke. Converting this equation to yield steam mass flowrate in BSPD-CWE gives $$W = 2.767 \frac{c^2 P}{X^{0.5}}, \tag{2}$$

where c is the choke bore diameter and W is the mass flowrate of wet steam. This equation can be generalized for a regression analysis data as $$W = a \frac{c^2 P}{X^b}, \quad (3)$$

where a and b are empirical constants determined from field data.

DEVELOPMENT OF ORIFICE PLATE 17 EQUATION

Equation (3) gives mass flowrate through choke 14 as a function of pressure and steam quality upstream of the choke inlet 17. Likewise, it becomes necessary to express mass flowrate through the orifice plate 17 as a function of the differential pressure drop across said orifice plate, and steam quality. The James[3] equation for the flow of wet steam through a sharp edged orifice can be expressed as $$W = \frac{24.65 C_o d^2 Y}{[1 - (d/D)^4]^{0.5}} \left( \frac{\phi}{X^{1.5}(v_g - v_f) + v_f} \right)^{0.5}. \quad (4)$$

In this equation, Co is the discharge coefficient; d is the diameter of the orifice plate; Y is the vapor expansion factor; $\phi$ is the differential pressure; D is the inside diameter of the meter run; X is the steam quality; $v_f$ and $v_g$ are the specific volumes of saturated water and steam at pressure P.

For steam qualities greater than 10%, the specific volume of water, $v_f$ is small relative to the specific volume of steam, $v_g$ and can therefore be neglected if one restricts the range of the device for measuring steam quality from 10% to 100%. For steam it has been determined that the specific volume of steam vapor, at pressures between 100 and 1000 psia, could be determined from $$v_6 = \frac{C_1}{P^{C_2}}, \quad (5)$$

| where: | $C_1$ | $C_2$ | P (psia) |
|---|---|---|---|
| | 376.204 | 0.9640 | 100–300 |
| | 486.340 | 1.0090 | 300–700 |
| | 783.514 | 1.0817 | 700–1000 |

Substituting equation (5) into equation (4) and assuming $v_f$ is small relative to $v_g$ gives $$W = \frac{24.65 C_o d^2 Y}{C_1(1 - (d/D)^4)^{0.5}} \left( \frac{\phi P^{C_2}}{X^{1.5}} \right)^{0.5}. \quad (6)$$

This equation expresses mass flowrate through a sharp edged orifice for pressure between 300 and 1000 psia, and steam quality between 10% ad 100%. Equation (6) can be written for higher pressure ranges by using an appropriate expressions for $C_1$ and $C_2$. We now have two algebraically simple expressions relating mass flowrate and steam quality through choke 14 with equation (3), and through the orifice plate 17 with equation (6).

SIMULTANEOUS SOLUTION OF EQUATIONS

Substituting equation (3) into equation (6) and solving for the steam quality, gives an expression for steam quality through the device as $$X = \left( \frac{607.62 C_o^2 (d/c)^4 Y^2 \phi}{C_1 a^2 [1 - (d/D)^4] P^{2-c_2}} \right)^{\frac{1}{1.5-2b}}, \quad (7)$$

where a and b are determined from experiments.

The vapor expansion factor Y corrects for the compressibility of steam which adiabatically expands as it passes through orifice plate 17. Determination of the vapor expansion factor Y can be made from the formula given by James[3].

$$Y = \sqrt{ r^{2/\gamma} \left( \frac{\gamma}{\gamma - 1} \right) \left( \frac{1 - r^{\frac{\gamma-1}{\gamma}}}{1 - r} \right) \left( \frac{1 - (d/D)^4}{1 - (d/D)^4 r^{2/\gamma}} \right) }$$

where $$r = \left( 1 + \frac{\phi}{27.692 P} \right)^{-1}$$

where
$\gamma = 1.3$

DESCRIPTION OF FIELD TEST

Equipment and Procedure

FIG. 1 shows a schematic view of the meter run used in the 2-inch steam line from a 5.8 MMBtu/hr Baker-Clayton steam generator used in a field test. The meter run consisted of a Daniels M 30 RW, 2-inch meter tube with inline straightening vanes upstream of a one-inch, Daniels ⅛-inch thick sharp edged orifice plate. Downstream of the flange connected orifice plate was a Thornhill-Craver critical flow choke assembly which incorporated interchangeable flow beans with bore diameters from 21 to 44–64ths of an inch. Between the orifice plate and the choke, the absolute pressure was measured with an ITT Barton Model 6005 pressure transmitter while the differential pressure across the orifice plate was measured with an ITT Barton Model 6001 differential pressure transmitter. The positioning of the orifice plate and straightening vanes in the meter run were according to the A.G.A. piping installation code for a 2-inch meter run.

A total of 20 test points were planned covering steam mass flowrates from 200 to 800 BSPD-CWE. At each of these steam rates, steam qualities of 20%, 40%, 60%, and 80% were used. Choke beans were sized to achieve these design rates and qualities by assuming a 500 psia pressure upstream of the choke. Once the feedwater flowrate through the generator was established using a positive displacement pump, the fuel rate to the generator was adjusted to achieve a given steam quality. The steam quality Xm from the generator was determined by measuring the conductivity of feedwater entering the generator $C_f$ and the conductivity of condensed steam $C_s$ with a portable Myron type L deluxe Model 532 conductivity meter. From these measurements, the steam quality being discharged from the generator was determined from $$X_m = 1 - C_f/C_s \quad (8)$$

The steam quality from the generator was also determined by measuring the mass flow rate of feedwater entering the generator and the static and differential pressure across an orifice plate in the discharge line from the generator. For a measured mass flow rate through the orifice plate, the James equation was used to calculate the reference steam quality. Predicted steam quality from the orifice/choke device was then compared to this reference steam quality.

TEST DATA

In a test to demonstrate the disclosed method, a total 29 test points were taken. Of these, 11 were eliminated because of instability of the generator at the times these points were taken. The remaining 110 data points are shown in Table 1. Data recorded for each test point were the bean diameter, pressure between the orifice plate and the choke, calibration steam quality from the orifice plate and measured flow rate, feedwater volumetric flowrate, orifice diameter and differential pressure across the orifice plate. Orifice plate sizes of 1-, 1.5- and 1.5-inches were used throughout the test.

Instability of the steam generator was detected due to large fluctuations in discharge pressure and feedwater rate. These fluctuations may have resulted from improper combustion in the generator, unexpected low backpressure, or lack of dampening of the feedwater positive displacement pump.

TABLE I

TEST DATA

| No. | Pressure (psig) | Differential Pressure (in. w.c.) | Feedwater Rate (bwpd) | Bean Size (64ths in.) | Orifice Diameter (in.) | Steam Quality (fraction) |
|---|---|---|---|---|---|---|
| 1 | 450.4 | 34.3 | 215.5 | 21 | 1.00 | 0.2951 |
| 2 | 455.4 | 34.2 | 208.6 | 21 | 1.00 | 0.3113 |
| 3 | 522.1 | 45.4 | 187.2 | 21 | 1.00 | 0.4902 |
| 4 | 659.4 | 72.4 | 194.1 | 21 | 1.00 | 0.7622 |
| 5 | 333.7 | 56.5 | 297.0 | 26 | 1.00 | 0.2191 |
| 6 | 334.8 | 53.0 | 298.0 | 26 | 1.00 | 0.2080 |
| 7 | 508.3 | 110.4 | 299.2 | 26 | 1.00 | 0.4626 |
| 8 | 515.1 | 111.8 | 297.3 | 26 | 1.00 | 0.4755 |
| 9 | 629.4 | 164.0 | 304.0 | 26 | 1.00 | 0.6944 |
| 10 | 615.3 | 162.0 | 310.0 | 26 | 1.00 | 0.6591 |
| 11 | 660.7 | 190.7 | 304.9 | 26 | 1.00 | 0.7944 |
| 12 | 654.7 | 182.8 | 314.9 | 26 | 1.00 | 0.7328 |
| 13 | 315.8 | 83.0 | 371.8 | 30 | 1.00 | 0.2008 |
| 14 | 601.2 | 254.1 | 406.0 | 30 | 1.00 | 0.6059 |
| 15 | 611.9 | 258.7 | 406.0 | 30 | 1.00 | 0.6214 |
| 16 | 603.5 | 254.9 | 406.3 | 30 | 1.00 | 0.6083 |
| 17 | 687.0 | 324.9 | 415.2 | 30 | 1.00 | 0.7654 |
| 18 | 682.2 | 326.8 | 415.5 | 30 | 1.00 | 0.7638 |
| 19 | 679.1 | 325.9 | 416.6 | 30 | 1.00 | 0.7571 |
| 20 | 324.0 | 108.8 | 516.9 | 32 | 1.00 | 0.1493 |
| 21 | 510.9 | 257.9 | 508.2 | 32 | 1.00 | 0.3951 |
| 22 | 503.5 | 254.6 | 510.1 | 32 | 1.00 | 0.3853 |
| 23 | 370.8 | 184.3 | 598.8 | 35 | 1.00 | 0.1949 |
| 24 | 362.0 | 169.8 | 602.9 | 35 | 1.00 | 0.1781 |
| 25 | 490.4 | 341.0 | 589.8 | 35 | 1.00 | 0.3766 |
| 26 | 489.9 | 332.4 | 592.9 | 35 | 1.00 | 0.3667 |
| 27 | 342.9 | 7.6 | 224.8 | 21 | 1.25 | 0.1542 |
| 28 | 348.4 | 8.2 | 203.3 | 21 | 1.25 | 0.1948 |
| 29 | 444.9 | 13.9 | 194.7 | 21 | 1.25 | 0.3605 |
| 30 | 594.4 | 23.8 | 213.9 | 21 | 1.25 | 0.5640 |
| 31 | 305.0 | 14.6 | 270.9 | 25 | 1.25 | 0.1797 |
| 32 | 307.9 | 15.5 | 267.5 | 25 | 1.25 | 0.1931 |
| 33 | 485.7 | 34.3 | 320.6 | 25 | 1.25 | 0.3551 |
| 34 | 486.1 | 33.8 | 320.6 | 25 | 1.25 | 0.3515 |
| 35 | 588.4 | 47.8 | 287.0 | 25 | 1.25 | 0.6044 |
| 36 | 597.5 | 48.8 | 283.8 | 25 | 1.25 | 0.6297 |
| 37 | 320.3 | 32.2 | 407.0 | 29 | 1.25 | 0.1815 |

Note:
The inside diameter of the meter run was 2.067-inches for all tests. The steam quality shown is calculated using a Co of 0.61 and the measured feedwater rate.

DISCUSSION OF RESULTS

Using the data in Table 1, an exponential least squares analysis of equation (3) yielded the following empirical constants:

$$a = 2.5253 \quad (9a),$$

and $$b = 0.466 \quad (9b).$$

Figure 3:
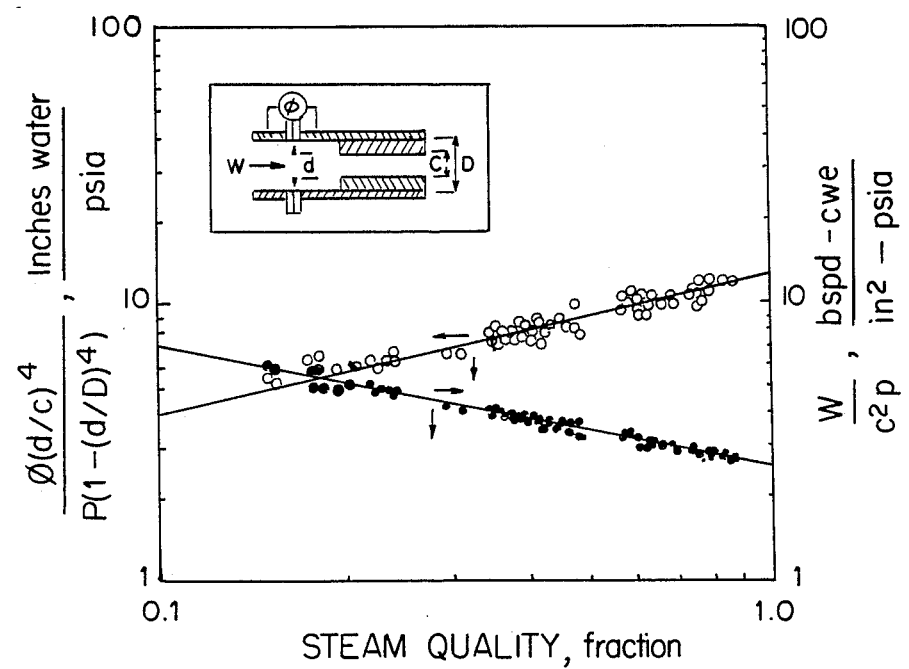
FIG. 3 is a graphical representation of steam quality.

FIG. 3 shows a plot of critical mass flowrate divided by pressure and choke bore diameter squared as a function of measured steam quality for the test data and equation (3) using these constants. Solving equation (7) for the discharge coefficient Co of the orifice plate for each test point in Table 1 using equations (9a) and (9b) gave an average discharge coefficient of $$C_o = 0.60 \quad (10).$$

Therefore, the final empirical equations for steam quality and mass flowrate are $$X = \left( \frac{95.28 C_o^2 (d/c)^4 Y^2 \phi}{C_1 [1 - (d/D)^4] P^{2-c_2}} \right)^{1.7606}, \quad (11)$$

and $$W = 2.5253 \frac{c^2 P}{X^{0.466}}, \quad (12)$$

where P is between 300 and 800 psia, and steam quality X is between 15% and 88%.

Table 2 shows the measured steam quality and mass flowrate compared with the predicted values using the above equations for each test point. The average steam quality deviation was ±4.6 quality points or an average percent error of 12.6%. The average mass flowrate deviation was ±31.9 BSPD-CWE or an average percent error of 8.7%. The data of Tables 1 and 2 show the measured versus predicted steam quality and steam mass flowrate for the test data.

It is understood that although modifications and variations of the invention can be made without departing from the spirit and scope thereof, only such limitations should be imposed as are indicated in the appended claims.

TABLE II

MEASURED VERSUS PREDICTED STEAM QUALITY AND FLOWRATE

| No. | Measured Steam Quality (%) | Predicted Steam Quality (%) | Measured Flowrate (Bspd-cwe) | Predicted Flowrate (Bspd-cwe) |
|---|---|---|---|---|
| 1 | 29.5 | 31.9 | 216 | 211 |
| 2 | 31.1 | 31.2 | 209 | 215 |
| 3 | 49.0 | 40.0 | 187 | 220 |
| 4 | 76.2 | 59.5 | 194 | 231 |
| 5 | 21.9 | 28.3 | 297 | 255 |
| 6 | 20.8 | 25.4 | 298 | 269 |
| 7 | 46.3 | 43.8 | 299 | 315 |
| 8 | 47.5 | 43.8 | 297 | 319 |
| 9 | 69.4 | 59.6 | 304 | 338 |
| 10 | 65.9 | 60.6 | 310 | 328 |
| 11 | 79.4 | 70.6 | 305 | 329 |
| 12 | 73.3 | 66.9 | 315 | 334 |
| 13 | 20.1 | 22.5 | 372 | 357 |
| 14 | 60.6 | 50.8 | 406 | 462 |
| 15 | 62.1 | 50.9 | 406 | 470 |

TABLE II-continued
MEASURED VERSUS PREDICTED STEAM QUALITY AND FLOWRATE

| No. | Measured Steam Quality (%) | Predicted Steam Quality (%) | Measured Flowrate (Bspd-cwe) | Predicted Flowrate (Bspd-cwe) |
| --- | --- | --- | --- | --- |
| 16 | 60.8 | 50.8 | 406 | 464 |
| 17 | 76.5 | 61.3 | 415 | 484 |
| 18 | 76.4 | 62.6 | 416 | 477 |
| 19 | 75.7 | 62.8 | 417 | 474 |
| 20 | 14.9 | 22.0 | 517 | 421 |
| 21 | 39.5 | 43.9 | 508 | 479 |
| 22 | 38.5 | 43.9 | 510 | 472 |
| 23 | 19.5 | 23.2 | 599 | 559 |
| 24 | 17.8 | 21.1 | 603 | 570 |
| 25 | 37.7 | 40.5 | 590 | 571 |
| 26 | 36.7 | 39.0 | 593 | 580 |
| 27 | 15.4 | 20.7 | 225 | 196 |
| 28 | 19.5 | 22.8 | 203 | 191 |
| 29 | 36.0 | 37.0 | 195 | 195 |
| 30 | 56.4 | 56.7 | 214 | 213 |
| 31 | 18.0 | 23.0 | 271 | 237 |
| 32 | 19.3 | 25.0 | 268 | 231 |
| 33 | 35.5 | 45.1 | 321 | 275 |
| 34 | 35.2 | 44.0 | 321 | 278 |
| 35 | 60.4 | 57.4 | 287 | 298 |
| 36 | 63.0 | 58.0 | 284 | 301 |

PUBLICATIONS REFERRED TO

1. Hawkins, G. A.: "Thermal Properties of Substances and Thermodynamics," Mark's Standard Handbook for Mech. Engr., Eighth Edition, pp. 4.46-4.49.
2. King, R. C. and Crocker, S.: Piping Handbook, Section 3, McGraw-Hill, New ork, 1967, p. 3-59.
3. James, R.: "Metering of Steam-Water Two Phase Flow by Sharp Edged Orifices," Proceedings Inst. Mech. Engr., Vol. 180, pt. 1, no. 23, 1965-1966, pp. 549-566.

We claim:

1. Apparatus for determining the mass flow rate and the quality of pressurized steam flowing through a conduit which comprises
    a choke member in said conduit having a flow passage of a diameter to constrict the flow of steam in the conduit to critical flow,
    an orifice plate in said conduit positioned upstream of said choke member to define an intermediate passage, and having an orifice diameter therethrough,
    means for measuring the pressure differential across said orifice plate,
    means for measuring the steam pressure in said intermediate passage, and
    means for determining the mean flow rate and the quality of the steam in said conduit in accordance with said pressure differential across the orifice plate and the pressure in said intermediate passage.
2. Apparatus as defined in claim 1 wherein the mean flow rate and the steam quality are determined in accordance with the formulae $$X = \left( \frac{95.28 C_o^2 (d/c)^4 Y^2 \phi}{C_1[1 - (d/D)^4] P^{2-c2}} \right)^{1.7606}$$

and $$W = 2.5253 \frac{c^2 P}{X^{0.466}}$$

wherein:
  $C_o$ = discharge coefficient of orifice plate
  d = diameter of orifice plate (inches)
  c = choke bore diameter (inches)
  Y = steam vapor expansion factor
  $\phi$ = differential pressure across the orifice plate (inches of water)
  D = inside diameter of meter run (inches)
  P = absolute pressure upstream of choke (psia)
  X = steam quality upstream of choke.

3. Apparatus as defined in claim 1 including steam flow control means in said conduit upstream of said orifice plate, being adjustable to regulate the steam flow rate upstream of said orifice plate.

4. Method for determining the quality and the mass flow rate of pressurized steam moving through a conduit, which conduit includes a choke having a constricted passage of sufficient size to give the pressurized steam critical flow characteristics, which method includes the step of
    positioning an orifice plate in said conduit upstream of the choke to define a space therebetween,
    determining a first pressure value in said conduit in said space between the orifice plate and choke,
    determining a second pressure value indicative of the differential in pressure across said orifice plate, and
    computing said mass flow rate and said steam quality as a function of said first and second pressure values.

5. In the method as defined in claim 6 wherein said computing step is achieved through application of the equation $$X = \left( \frac{95.28 C_o^2 (d/c)^4 Y^2 \phi}{C_1[1 - (d/D)^4] P^{2-c2}} \right)^{1.7606}$$

and $$W = 2.5253 \frac{c^2 P}{X^{0.466}}$$

x is the steam quality and wherein:
  w is mass rate of flow
  $C_o$ = discharge coefficient of orifice plate
  d = diameter of orifice plate (inches)
  c = choke bore diameter (inches)
  Y = steam vapor expansion factor
  $\phi$ = differential pressure across the orifice plate (in. of water)
  D = inside diameter of meter run (inches)
  P = absolute pressure upstream of choke (psig)
  x = steam quality upstream of choke.

* * * * *